United States Patent
Li et al.

(10) Patent No.: US 9,380,984 B2
(45) Date of Patent: Jul. 5, 2016

(54) COMPUTER TOMOGRAPHY IMAGING DEVICE AND METHOD

(75) Inventors: Liang Li, Beijing (CN); Zhiqiang Chen, Beijing (CN); Li Zhang, Beijing (CN); Kejun Kang, Beijing (CN); Yuanjing Li, Beijing (CN); Yinong Liu, Beijing (CN); Yuxiang Xing, Beijing (CN); Ziran Zhao, Beijing (CN)

(73) Assignees: TSINGHUA UNIVERSITY, Beijing (CN); NUCTECH COMPANY LIMITED, Beijing (CN)

( * ) Notice: Subject to any disclaimer, the term of this patent is extended or adjusted under 35 U.S.C. 154(b) by 0 days.

(21) Appl. No.: 13/322,696

(22) PCT Filed: Dec. 30, 2009

(86) PCT No.: PCT/CN2009/001593
§ 371 (c)(1),
(2), (4) Date: Feb. 27, 2012

(87) PCT Pub. No.: WO2010/135855
PCT Pub. Date: Dec. 2, 2010

(65) Prior Publication Data
US 2012/0140874 A1  Jun. 7, 2012

(30) Foreign Application Priority Data
May 26, 2009 (CN) .......................... 2009 1 0085612

(51) Int. Cl.
*G06T 11/00* (2006.01)
*A61B 6/03* (2006.01)
(Continued)

(52) U.S. Cl.
CPC . *A61B 6/032* (2013.01); *A61B 6/06* (2013.01); *A61B 6/4452* (2013.01); *A61B 6/469* (2013.01);
(Continued)

(58) Field of Classification Search
CPC .............................. G06T 11/003; G06T 11/006
USPC ................................................ 378/4; 382/131
See application file for complete search history.

(56) References Cited

U.S. PATENT DOCUMENTS 5,323,007 A * 6/1994 Wernick et al. .......... 250/363.03
5,724,400 A   3/1998 Swerdloff et al.
(Continued)

FOREIGN PATENT DOCUMENTS

CN  1419893 A    5/2003
CN  101023448 A  8/2007

OTHER PUBLICATIONS

European Office Action for EP Application No. 09845074.5 dated Nov. 19, 2015.
(Continued)

*Primary Examiner* — Thomas R Artman
(74) *Attorney, Agent, or Firm* — Randall G. Rueth

(57) ABSTRACT

The present invention discloses a method for performing CT imaging on a region of interest of an object under examination, comprising: acquiring the CT projection data of the region of interest; acquiring the CT projection data of region B; selecting a group of PI line segments covering the region of interest, and calculating the reconstruction image value for each PI line segment in the group; and combining the reconstruction image values in all the PI line segments to obtain the image of the region of interest. The present invention further discloses a CT imaging device using this method and a data processor therein. Since the 2D/3D slice image of the region of interest can be exactly reconstructed and obtained as long as the X-ray beam covers the region of interest and the region B, it is possible to use a small-sized detector to perform CT imaging on the region of interest at any position of a large-sized object, which reduces to a great extent the radiation dose of the X-ray during the CT scanning.

13 Claims, 6 Drawing Sheets

(51) Int. Cl.
*A61B 6/06* (2006.01)
*A61B 6/00* (2006.01)

(52) U.S. Cl.
CPC ......... *G06T 11/006* (2013.01); *G06T 2211/416* (2013.01); *G06T 2211/421* (2013.01); *G06T 2211/424* (2013.01)

(56) References Cited

U.S. PATENT DOCUMENTS

| | | | |
|---|---|---|---|
| 6,385,278 | B1 | 5/2002 | Hsieh |
| 6,835,278 | B2 | 12/2004 | Selbrede et al. |
| 6,891,178 | B2 * | 5/2005 | Xing ........................ 250/505.1 |
| 2002/0141534 | A1 * | 10/2002 | Mizobuchi et al. ............. 378/54 |
| 2004/0109529 | A1 * | 6/2004 | Eberhard et al. ................ 378/23 |
| 2005/0249432 | A1 * | 11/2005 | Zou et al. ...................... 382/276 |
| 2006/0291611 | A1 * | 12/2006 | Pack et al. .......................... 378/4 |
| 2008/0013676 | A1 * | 1/2008 | Bontus et al. ................... 378/17 |
| 2008/0118032 | A1 | 5/2008 | Graham et al. |
| 2008/0205597 | A1 * | 8/2008 | Ono ................................ 378/65 |
| 2011/0052021 | A1 * | 3/2011 | Noo et al. ...................... 382/131 |
| 2011/0105880 | A1 * | 5/2011 | Yu et al. ........................ 600/407 |
| 2011/0170757 | A1 * | 7/2011 | Pan et al. ...................... 382/131 |

OTHER PUBLICATIONS

Faridani, A., et al., "Local Tomography," *SIAM Journal on Applied Mathematics*. 1992, vol. 52, pp. 459-484. http://links.jstor.org/sici?sici=0036-1399%28199204%2952%3A2%3C459%3ALT%-3E2.0.CO%3B2-f.

Katsevich, A., et al., "Pseudolocal Tomography," *SIAM Journal on Applied Mathematics*. 1996, vol. 56, pp. 167-191. http://links.jstor.org/sici?sici=0036-1399%28199602%2956%3A1%3-C167%3APT%3E2.0.CO%3B2-4.

Katsevich, A., "A General Scheme for Constructing Inversion Algorithms for Cone Beam CT," *International Journal of Mathematics and Mathematical Science*. 2003, vol. 21, pp. 1305-1321.

Katsevich, A., "An Improved Exact Filtered Backprojection Algorithm for Spiral Computed Tomography," *Advances in Applied Mathematics*. 2004, vol. 32, pp. 681-697.

Zou, Y., et al., "Exact Image Reconstruction on PI-lines From Minimum Data in Helical Cone-Beam CT," *Physics in Medicine and Biology*. 2004, vol. 49, pp. 941-959.

Zou, Y., et al., "Image reconstruction on PI-lines by use of filtered backprojection in helical cone-beam CT," *Physics in Medicine and Biology*. 2004, vol. 49, pp. 2717-2731.

Defrise, M., et al., "Truncated Hilbert Transform and Image Reconstruction From Limited Tomographic Data," *Inverse Problems*. 2006, vol. 22, 1037-1053.

Ye, Y.B., et al., "A General Local Reconstruction Approach Based on a Truncated Hilbert Transform," *International Journal of Biomedical Imaging*. 2007, vol. 2007, Article ID 63634.

Li, Liang, "A Transform Theory of CT Projections and Cone-Beam Image Reconstruction" [dissertation], Doctor of Engineering, Tsinghua University, Beijing, 2007.

Li, Liang, et al., "3D Region-of-Interest (ROI) Reconstruction from Truncated Data in Circular Cone-beam CT," *IEEE Nuclear Science Symposium Conference Record*. Oct. 2008, pp. 5144-5145.

Li, Liang, et al., "Region-of-Interest Image Reconstruction Algorithms and Numerical Experiments," *Computerized Tomography Theory and Applications*, Tsinghua University (Department of Engineering Physics), Beijing. 2009, vol. 18, pp. 1-7.

Li, Liang, et al., "A General Region-of-Interest Image Reconstruction Approach With Truncated Hilbert Transform," *Journal of X-ray Science and Technology*. 2009, vol. 17, Issue 2, pp. 135-152.

Li, Liang, et al., "New Development of Interior Region-of-Interest CT Accurate Reconstruction Algorithm," National Ray Digital Imaging and New Technology of CT Seminar Symposium. Jun. 2009, p. 81.

International Search Report in International Application No. PCT/CN2009/001593, dated Mar. 18, 2010 (English translation).

\* cited by examiner

COMPUTER TOMOGRAPHY IMAGING DEVICE AND METHOD

CROSS-REFERENCE TO RELATED APPLICATIONS

This is the U.S. national phase of International Application No. PCT/CN2009/001593, filed Dec. 30, 2009, which claims the benefit of Chinese Patent Application No. 200910085612.4, filed May 26, 2009.

TECHNICAL FIELD

The present invention relates to a computer tomography (CT) imaging device, in particular to a device for CT imaging of a region of interest (ROI), and a CT imaging method for use in the such devices as well as a computer program product and a recording medium for implementing the imaging method.

BACKGROUND ART

CT technology has brought revolutionary impact on medical diagnosis and industrial nondestructive testing even since Hounsfield has invented the first CT machine in 1972, and CT has been one of the important detection measures in the industries of medical treatment, biology, aeronautics and astronautics, national defense, etc. X-ray cone-beam CT has been widely used in the fields of clinical medicine, security check, nondestructive detection, etc. Especially in medical and clinical diagnosis, spiral CT has been one of the indispensable measures for examination[1].

Although CT technology has currently achieved great success in the fields of industry, security check, medical care and so on, due to the complexity and the diversity of engineering application conditions, high requirements are put forth for further development of CT technology. In particular, in the industrial application, CT technology faces with many difficulties in terms of large-sized imaging with high accuracy and medical imaging with low dose, etc. This is mainly because: the CT scanning field of view (FOV) is restricted by the width of the X-ray beam, the size of the detector and the angle of the view, which gives rise to the possibility that the projection data of the scanning of a large object has truncations in the two directions of the detector and the scanning angle; the current mainstream CT algorithms are all overall reconstruction methods with respect to an intact object, which require the X-ray beam to cover the slices of the object completely and can hardly deal with the occasion where the projection data is truncated. Therefore, when imaging a large object or an irregular object, it is often difficult to perform the scanning directly, but instead, the ultimate image can only be reconstructed with approximate conversion methods such as data rearrangement after many times of scanning, which affects the speed and the accuracy of CT image adversely.

In addition, the detector of a CT device has been the key factor that influences the hardware cost of the CT device, and the price of the detector is directly proportional to the size and amount of the detector units. However, the price of detector remains high, which greatly limits the cost margin of CT products.

On the other hand, in medical CT imaging, in order to ensure that the projection data of the X-ray is not truncated, the width of the X-ray beam for use in the current CT scanning must cover the width of the slices of the human body, however, the real interest region often only relates to a certain organ of the human body, and as a result, an unnecessary radiation dose on the human body during the CT scanning is greatly increased. If the present way of CT design is not changed, the radiation dose can hardly be reduced. At present, medical irradiation has been the largest artificial ionizing radiation source for the human being, and hence reducing the X-ray dose during CT examination has become a significant subject concerning the health of the entire public and the posterities of the society.

Moreover, increasing requirements are put forth for the medical diagnosis. In particular, the medical diagnosis of some special body parts, such as female breast, cochlea, teeth and so on, requires high spatial resolution. In this regard, currently mainstream whole body spiral CT machine cannot meet the requirements for a normal medical diagnosis. With the rapid development of large-area flat-panel detector techniques, the medical flat-panel detector techniques have been mature enough for being applied in X-ray DR imaging with high spatial resolution. The flat-panel detector based on amorphous selenium and amorphous silicon techniques now has a detector aperture of larger than 500 mm×500 mm, and a pixel size of about 0.1 mm, whereas the detector of multilayered spiral CT has only a unit size of about 0.5 mm, so flat-panel detector can achieve CT images with much higher spatial resolutions compared with the spiral CT. However, due to the huge amount of data from the flat-panel detector, the data transmission speed still cannot meet the requirements for cone-beam CT imaging, and there are no CT devices using flat-panel detectors for whole body imaging in the practice. If we are not directed at the entire human body, but at the organs of interest with small-scaled flat-panel detectors to achieve CT imaging of the region of interest with high accuracy, it is possible that the technical bottleneck of slow data transmission could be broken.

With regard to the disadvantages and limitations of the CT system, we started to explore new CT imaging reconstruction methods and CT imaging modes. In fact, in many engineering applications, an overall CT imaging of the intact object is not required, but instead, only the imaging of the object in a certain region of interest (ROI) is needed. Especially in medical and clinical diagnosis, it is only necessary to image the part of the suspicious lesion[2].

At the beginning of the 1980s, the study of local CT imaging of an object has begun. Given the bondage of the CT reconstruction theories at that time, people could not precisely reconstruct the local CT image of the object, and hence resorted to a approximate function related to the slice image of the object. In 1985, Smith et al. proposed a local reconstruction algorithm of lambda tomography which reconstructs with the local projection data a function having the same singularity as the ROI density function[3]. Subsequently, Katsevich brought forward a local reconstruction algorithm of pseudolocal tomography which replaces the original function by reconstructing part of the Hilbert transform of the density function[4]. However, as these functions could not replace the real slice image of the object, they could hardly meet the requirements for real engineering applications, which greatly impaired the significance of local CT imaging in real engineering applications. Consequently, the study of local ROI imaging of an object had stagnated for a long term and could not find way out.

In the recent years, the CT reconstruction theory has witnessed huge progress. In 2002, Katsevich first put forth an exact reconstruction algorithm for cone-beam spiral CT based on the form of Filtered Back Projection (FBP). The algorithm solves well the problem of reconstructing long objects, and in case of projection data truncation in direction of the Z axis, it can still reconstruct the image of the object exactly for the scanned part. Besides, as the algorithm is in the form of FBP, it has considerable advantages over the iterative reconstruction algorithm in terms of reconstruction speed, so Katesevich provided a brand-new way of thinking for the development of CT algorithm[5-6]. In 2004, Zou and Pan brought forward an exact reconstruction algorithm for spiral CT in the form of Back Projection Filtration (BPF), which only requires theoretically minimum projection data to reconstruct the slice image of the object exactly[7-8]. Thus, the basic theoretical problems of spiral CT reconstruction have been solved appropriately. After that, the BPF algorithm has been widely applied to the CT image reconstruction of parallel beams, sector beams and cone beams. The BPF algorithm of Zou and Pan is a reconstruction algorithm based on the PI line, wherein the PI line is a line segment connecting any two points in the scanning trace, and wherein the BPF algorithm requires the two end points of each PI line to fall outside the support of the object. The greatest advantage of the algorithm lies in that the image in the PI line can still be reconstructed exactly when the projection data is somewhat truncated, which makes it possible to perform CT reconstruction with respect to the ROI instead of the intact object. In 2006, Defrise et al. obtained further achievements based on the BPF algorithm and eased the restriction of PI line by proving that when the PI line has only one end point outside the support of the object, the image in the PI line can still be reconstructed exactly with the projection data passing through the PI line[9]. In 2007, Wang et al. further proved that when the PI line completely falls within the object, the image of the object in the PI line can be reconstructed exactly with the truncated projection data if part of the image information in the PI line is known[10]. However, in real CT engineering applications, it is difficult to acquire information about the reconstruction values in the PI line inside the object in advance, so the method of Wang et al. has certain limitations in real applications.

RELATED DOCUMENTS

[1] Liang Li, A study of CT projection transform theory and cone-beam reconstruction [dissertation], Beijing: Department of Engineering Physics, Tsinghua University, 2007.
[2] Liang Li, Zhiqiang Chen, Kejun Kang, Li Zhang, Yuxiang Xing, "Region-of-interest Image Reconstruction Algorithms and Numerical Experiments", Computerized Tomography Theory and Applications, 18:1-7, 2009.
[3] A Faridani, E L Ritman, K T Smith. "Local tomography", SIAM Appl Math, 52: 459-484, 1992.
[4] A Katsevich, A. G. Ramm. "Pseudolocal tomography", SIAM Appl Math, 56: 167-191, 1996.
[5] Katsevich A. A general scheme for constructing inversion algorithms for cone beam CT. Int J Math Math Sci, 2003, 21:1305-1321.
[6] Katsevich A. An improved exact filtered backprojection algorithm for spiral computed tomography. Adv Appl Math, 2004, 32:681-697.
[7] Zou Y, Pan X. Exact image reconstruction on PI-lines from minimum data in helical cone-beam CT. Phys Med Biol, 2004, 49:941-959.
[8] Zou Y, Pan X. Image reconstruction on PI-lines by use of filtered backprojection in helical cone-beam CT. Phys Med Biol, 2004, 49:2717-2731.
[9] M Defrise, F Noo, R Clackdoyle, H Kudo. "Truncated Hilbert transform and image reconstruction from limited tomographic data", Inverse Problems, 22: 1037–1053, 2006.
[10] Y B Ye, H Y Yu, Y Wei, G Wang. "A General Local Reconstruction Approach Based on a Truncated Hilbert Transform", International Journal of Biomedical Imaging, Volume 2007, Article ID 63634.

CONTENTS OF THE INVENTION

The applicant of the present invention has developed a novel sufficiency condition of exact CT data reconstruction:

For a random point $\vec{r}_0=(\cos\phi_0, \sin\phi_0)$, the image function $f(\vec{r})$ can be reconstructed exactly if the projection data fulfills the following conditions at the same time:

1. There is a vector $\vec{n}=(-\sin\phi_0, \cos\phi_0)$ and two line segments $L_f \subset L$ and $L_0 \subset L$, wherein L is a line segment with the support of function $f(\vec{r})$, which passes point $\vec{r}_0$ and is parallel with $\vec{n}$, and wherein $\vec{r}_0 \in L_f$;
2. The line segment $L_0$ has at least one end point falling outside the support of the function, or $f(\vec{r})$ in the line segment $L_0$ is known;
3. For a random point $\vec{r} \in L_f \cup L_0$, the projection $p(s,\phi)$ at any angle $\phi \in [\phi_0, \phi_0+\pi]$ passing any point in the small neighborhood comprising the random point can be acquired, wherein $s=\vec{r} \cdot \vec{n}^\perp$.

The above conditions can be explained by FIG. 1. When the region of interest ROI falls within the support of the object, the ROI image cannot be reconstructed exactly with FOV only covering ROI, and additional projection information is needed for reconstructing the slice image of the ROI, and there are two groups of situations: (a) and (b) belong to one group of situations, i.e., an additional dark shadow region is added, and it is necessary that the projection data passing through the shadow region can be acquired, wherein the image of the dark shadow region is known; (c) and (d) belong to another group of situations, i.e., an additional shadow region B is added, and part or all of the region falls outside the support of the object. As long as either of the two groups of situations is satisfied, the exact CT imaging of the region of interest ROI can be achieved. Comparing the four situations in FIG. 1, we can find that as it is not necessary to know the image information about the additional shadow region in the latter two situations (c) and (d), it is more convenient to implement these two situations in engineering applications; especially in the last situation (d), since the shadow region B falls outside the support of the object, the slice image of the ROI can be reconstructed exactly as long as the X-ray projections passing through the ROI and the region B are measured, which means that with a medical imaging applying this CT scanning manner, the person to be detected can be exposed to less radiation dose. The person to be detected only needs to be exposed to a dose of X-ray scanning the region of the suspicious tissue and a dose of X-ray passing through a very little aerial region outside of the body, which can reduce to a great extent the radiation dose on the person to be detected compared with the current whole body spiral CT scanning.

The present invention is put forth based on the sufficiency condition of exact CT data reconstruction, in particular based on the situation (d). According to one aspect of invention, a method for CT imaging a region of interest of an object under examination is provided, comprising steps of: acquiring the CT projection data of the region of interest; acquiring the CT projection data of region B, wherein at least part of the region B falls outside the support of the object under examination and the region B is selected to enable the selection of a group of PI line segments covering the region of interest, wherein each PI line passing through the region of interest passes through the region B; and reconstructing the CT projection data of the region of interest in accordance with the CT projection data of both the region of interest and the region B.

According to a further aspect of the present invention, a CT imaging device for CT imaging the region of interest of an object under examination is provided, comprising: an X-ray generator for generating an X-ray beam for use in CT scanning; detectors for detecting the X-ray passing through the scanned region so as to generate projection data; carrier of the object under examination for carrying the object under examination moving in and out of the CT imaging device; a main controller for controlling the operation of the CT imaging device, such that the X-ray emitted from the X-ray generator only covers the region of interest so that the CT scanning is performed to obtain the projection data of the region of interest, and such that the X-ray emitted from the X-ray generator only covers the region B so that the CT scanning is performed to obtain the projection data of the region B, wherein at least part of the region B falls outside the support of the object under examination and the region B is selected to enable the selection of a group of PI line segments covering the region of interest, wherein each PI line passing through the region of interest passes through the region B; and a data processor for reconstructing the image of the region of interest in accordance with the obtained projection data of the region of interest and the region B.

The present invention further provides a computer program product comprising instructions for implementing the method steps of the CT imaging method of the present invention when loaded to a computer and operated thereon.

The present invention further provides a recording medium which stores instructions for implementing the method steps of the CT imaging method of the present invention when loaded to a computer and operated thereon.

According to the X-ray CT imaging device and method in the present invention, the 2D/3D slice image of a region of interest can be exactly reconstructed as long as the X-ray beam emitted from the X-ray source covers the region of interest, so it is possible to use a small-sized detector to perform CT imaging on the region of interest at any position of a large-sized object, which improves the speed of CT scanning and image reconstruction and cuts the hardware cost of a CT device, and meanwhile reduces to a great extent the radiation dose of the X-ray during the CT scanning. Therefore, the present invention is highly potential for market applications.

DESCRIPTION OF FIGURES

Other advantages and benefits of the present invention will be clear and obvious to those skilled in the art from the detailed description of the detail embodiments in the following. The drawings are only used for the purpose of showing the embodiments and should not be construed as limiting the invention. The same reference signs represent the same components throughout the drawings, specifically.

DETAIL DESCRIPTION

Further descriptions of the present invention are given as follows in combination with the figures and the specific embodiments.

Figure 1:
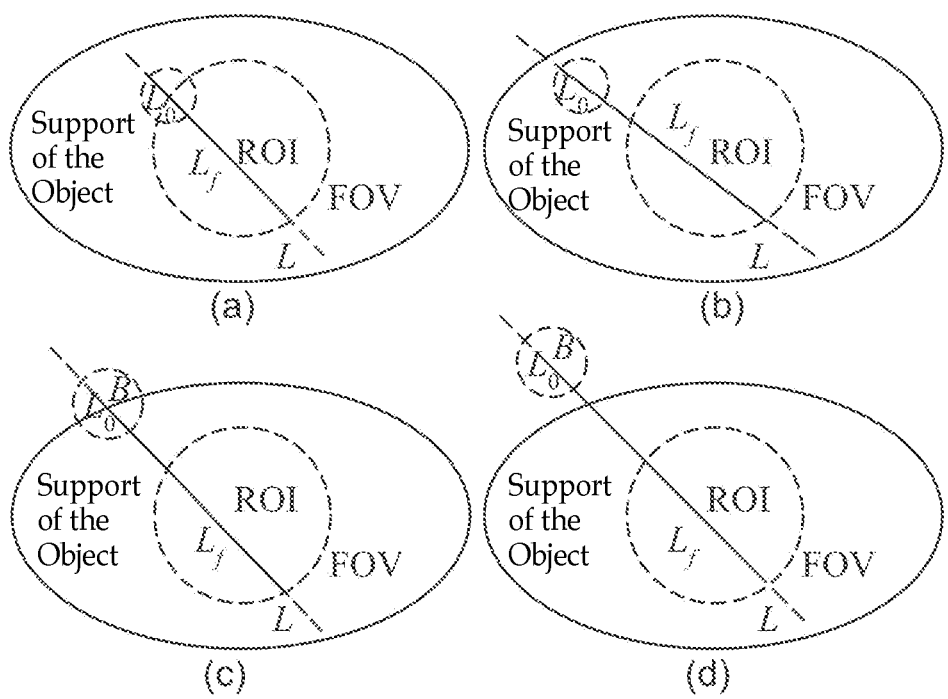
FIG. 1 shows a sufficiency condition of exact CT data reconstruction according to the present invention.
Figure 2:
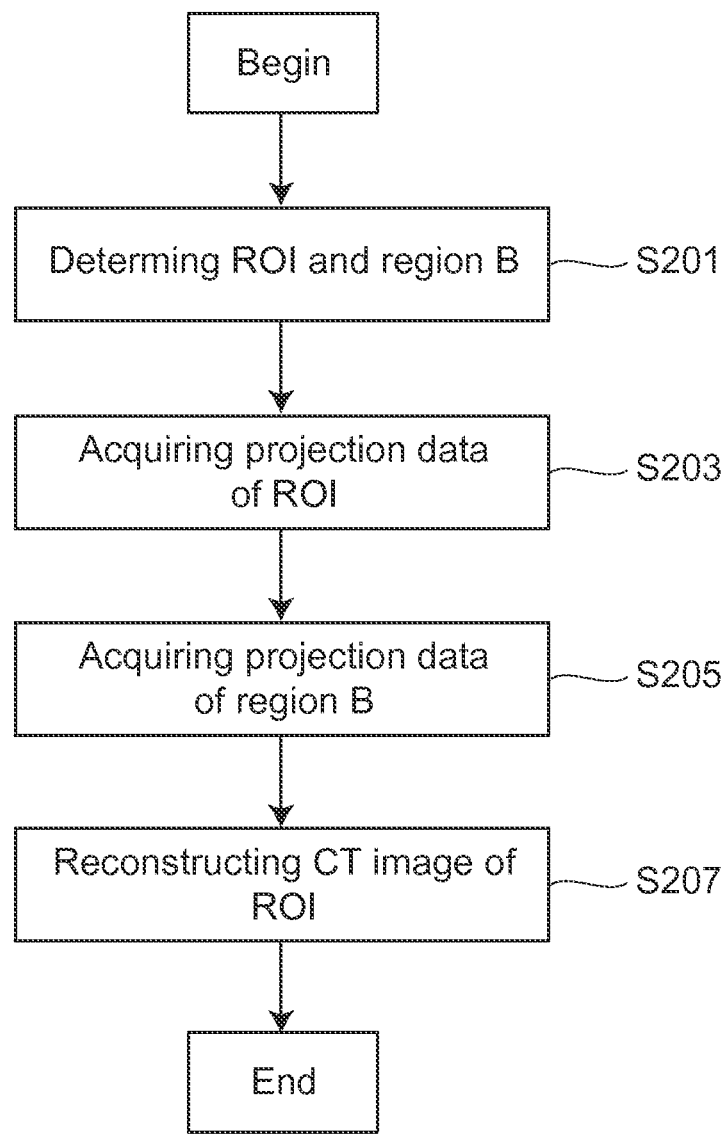
FIG. 2 describes a flow chart of the computer tomography (CT) imaging method according to an embodiment of the present invention.

As mentioned above in the situation (d) about a sufficiency condition of exact CT data reconstruction, to exactly reconstruct the slice image of ROI, it only requires the acquisition of the X-ray projections passing through the ROI and the region B by means of scanning FIG. 2 describes a computed tomography (CT) imaging method according to an embodiment of the present invention. In step S201, a region of interest (ROI) of an object under examination to be the CT imaging is determined, and a region B having at least a part falling outside the support of the object is determined based on the determined ROI. The region B is selected to enable a selection of a group of PI line segments covering the ROI, wherein each PI line passing through the ROI passes through the region B (as shown in FIG. 1 (d)). The region B can be a spatial region of any size and shape. Consideration of the two factors, that is, the size of the actual detector unit and the radiation dose on the patient, the region B can generally be selected as a circular or spherical spatial region with a diameter 10 times of that of the detector unit. Of course, there can be more than one region B. Besides, in order to further improve the speed and the accuracy of image reconstruction, other reference regions can be further determined.

After the ROI and the region B have been determined, in step S203, the ROI region is adjusted into the scanning field of view such that the X-ray beam for scanning only covers the ROI, and performs CT scanning for the ROI to acquire the CT projection data of the ROI. Then in step S205, the region B is adjusted into the scanning field of view such that the X-ray beam only covers the region B and performs CT scanning for the region B to acquire the CT projection data of the region B. Subsequently, in step S207, based on the CT projection data of the ROI acquired in step S203 and the CT projection data of the region B acquired in step S205, a CT image of the ROI is reconstructed according to the reconstruction method described in FIG. 3. In the CT imaging method of the present invention, although two times of CT scanning are involved in the reconstruction of the CT image for the ROI, in each scanning, the X-ray beam only covers the ROI or the region B, so the object under examination in the two times of scanning is exposed to a total X-ray radiation dose much less than that of a traditional CT scanning.

Figure 3:
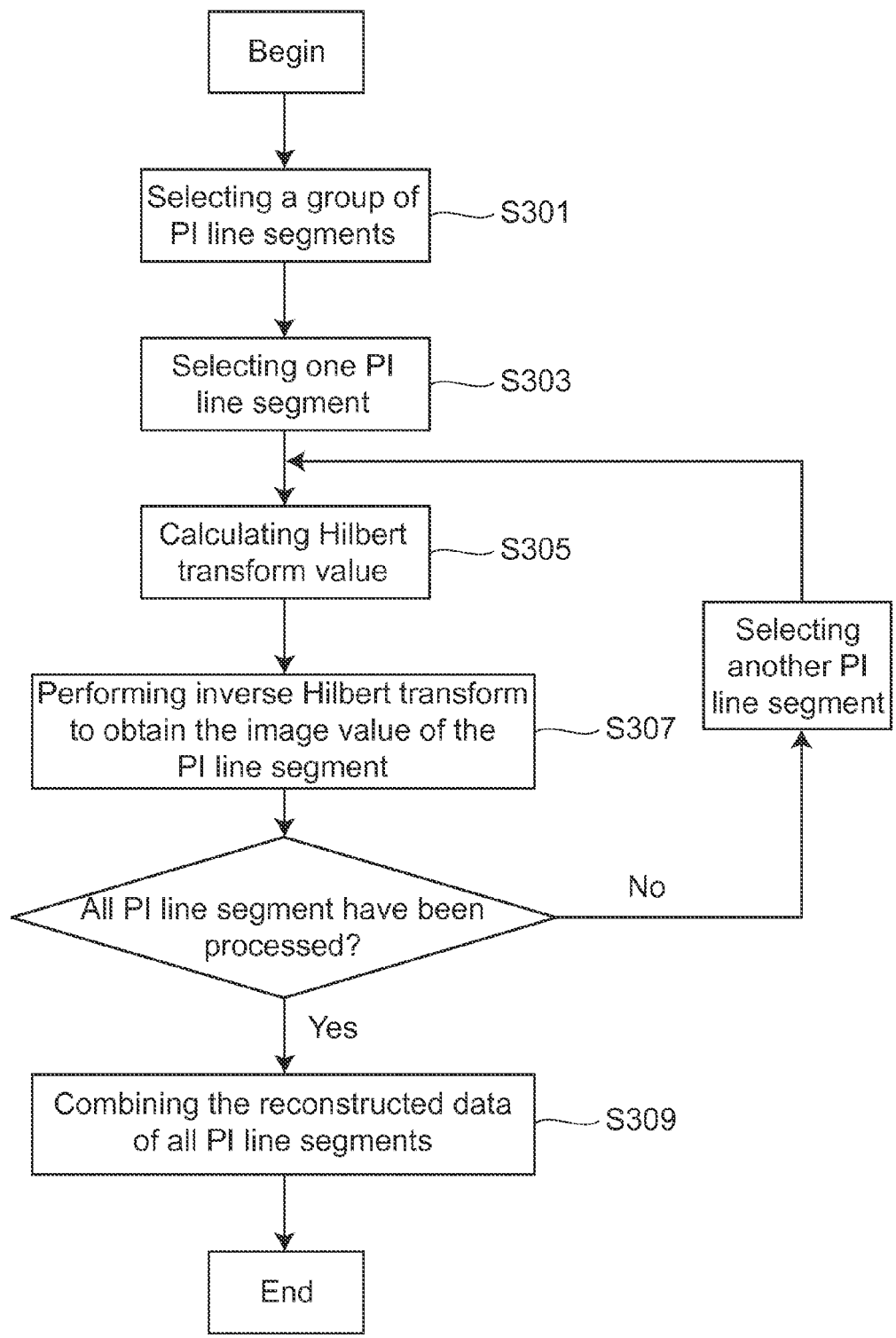
FIG. 3 describes a flow chart of the project data reconstruction method to be executed in the CT imaging method of FIG. 2 according to an embodiment of the present invention.

FIG. 3 specifically describes the reconstruction method executed in step S207 as shown in FIG. 2. In step S301, a group of PI line segments covering the ROI is selected, and it is ensured that each PI line passing through the ROI also passes through the region B.

Then it comes to steps S303-S307, wherein for each PI line in the group of PI line segments selected in step S301, image reconstruction is performed along the PI line. Subsequently, in step S309, the reconstruction data of all of PI lines are combined to obtain the result ROI image. The procedure of PI-line-based image reconstruction is the same in 2D and 3D reconstruction. Take an example by a 2D image reconstruction to explain the image reconstruction processing executed in steps S303-S307 based on a PI line.

A 2D image along a PI line is defined as function $f(\vec{r}) \in L^2(P)$, and thereby the image reconstruction processing is to seek for the intersection function fulfilling all the five constraints in formula (1).

$$C_1 = \{f \in L^2(P) | (Hf)(x) = g(x), x \in (a,b) \text{Å}(c,d)\}$$
$$C_2 = \{f \in L^2(P) | f(x) = f_0(x), x \in (a,b)\}$$
$$C_3 = \{f \in L^2(P) | \int_{-1}^{+1} dx f(x) = \pi C_f\}$$
$$C_4 = \{f \in L^2(P) | f(x) \geq 0, x \in [-1,1]\}$$
$$C_5 = \{f \in L^2(P) | f(x) \leq f_{max}, x \in [-1,1]\} \quad (1)$$

where $$C_f = \frac{1}{\pi} \int_{-1}^{+1} dx f(x)$$

can be obtained by directly calculating the measured CT projection data. In addition, $x \in [-1,1]$ represents a normalized one dimensional PI line segment, $x \in (a,b)$ is the part of the PI line segment within a region B falling outside the support of the object under examination, and (c,d) is the part of the PI line segment within the ROI, as shown in FIG. 1 (d).

$f_0(x)$ is an object image in the part of PI line segment within the region B, as it falls outside the support of the object under examination and is usually the air, the image reconstruction value is generally set as 0. $f_{max}$ represents the possible maximum value in the reconstructed image which can be set as an attenuation coefficient value of the material in the object having the maximum density according to the property of the object. For instance, in a medical CT imaging, the object under examination is usually human beings and the maximum value of the reconstructed image is generally that of the bone tissues, so $f_{max}$ can be set as an attenuation coefficient value of the bone tissues under corresponding X-ray energy. g(x) is a one dimensional Hilbert transform value in the PI line segment, i.e., the result of difference calculation of the projection data and then back projection to the PI line segment, which can be calculated by the following formula:

$$b(\vec{r}_0) = -\frac{1}{2\pi} \int_{\phi_0}^{\phi_0+\pi} d\phi \frac{\partial p(s,\phi)}{\partial s} \bigg|_{s=\vec{r}_0 \cdot \vec{u}(\phi)} \quad (2)$$

where $\vec{r}$ is a two dimensional coordinate representation in the slice image space of a point in the one dimensional PI line and represents as $\vec{r} = (\cos \phi_0, \sin \phi_0)$, and in one-to-one correspondence with the point x in g(x), wherein p(s,φ) represents the projection data, s is the one dimensional coordinate in the detector, φ is the angle of the projection, $\vec{u}(\phi) = (\cos \phi, \sin \phi)$. In this case, g(x) and $b(\vec{r}_0)$ have the same meaning, and are only represented as different variants as they are in different coordinate systems.

It may be easy to understand and to implement the constraint conditions $C_2, C_4, C_5$ in formula (1), and condition $C_1$ can be implemented by POCS (Projection onto Convex Set) iterative calculation. Specifically, condition $C_1$ can be implemented by the following iterative calculation:

$$f^k(x) = H^{-1} \tilde{g}^k(x), k=1,2,3 \quad (3)$$

where $f^k(x)$ represents the intermediate reconstruction image of the iteration, and k represents the iterative step. The initial image $f^0(x)$ of the iteration can be an arbitrary estimate and set artificially, generally as all-zero. $H^{-1}$ denotes the inverse Hilbert transform, and the transform formula is:

$$H^{-1} g(x) = -\frac{1}{\pi} P.V. \int_{-1}^{+1} \frac{dt}{t} g(x-t) \quad (4)$$

where P.V. represents the Cauchy principal value integral. $\tilde{g}^k(x)$ in formula (3) is defined as:

$$\tilde{g}^k(x) = \begin{cases} g(x), x \in (a,b) \cup (c,d) \\ (Hf^{k-1})(x), x \in [-1,a] \cup [b,c] \cup [d,1] \end{cases} \quad (5)$$

where g(x) is calculated from the preceding formula (2), and during the POCS iterative procedure, it remains constant without back projection iterative computations.

The formula for calculating the constraint condition $C_3$ in formula (1) is:

$$f^k(x) = \begin{cases} f_0(x), x \in (a,b) \\ f^{k-1}(x) + \frac{\pi C_f - \int_a^b dx' f_0(x')}{(2+a-b)} \\ -\frac{\left(\int_{-1}^a + \int_b^1\right) dx' f^{k-1}(x')}{(2+a-b)}, x \in [-1,a] \cup [b,1] \end{cases} \quad (6)$$

Based on the description of the specific processing of solving formula (1), it can be known that in the seeking for the intersection function fulfilling all the five constraints in formula (1), it is necessary to perform back projection filtration first (i.e., to acquire the value of g(x)), and then to acquire the value of $f(\vec{r})$ by POCS iterative calculation. AS the POCS iterative procedure is always a repeated iteration between the reconstruction image domain and the Hilbert transform space and there is no problem of forward projection, the speed of image reconstruction is very fast.

Specifically, in step S303, one PI line segment is selected from the group of PI line segments. Then in step S305, a one dimensional Hilbert transform value of the selected PI line segment is calculated, which can be obtained in accordance with formula (2). Subsequently, in step S307, limit inverse Hilbert transform is performed for the one dimensional Hilbert transform value calculated in step S305 to acquire the reconstruction image value of the PI line segment. In the processing of step S307, a repeated iteration, i.e., the POCS iterative procedure, between the reconstruction image domain and the Hilbert transform space domain is required to acquire a reconstruction image satisfying the accuracy requirement. The processing of step S307 can be performed in accordance with formulas (1) and (3)-(6).

It should be noted that the above reconstruction method is not limited to a certain scanning manner, and it can be applicable to the CT scanning using parallel beam, sector beam or cone beam X-ray. Meanwhile, the reconstruction method is also applicable to different scanning traces, and the only difference lies in that the back projection formula (2) may change slightly in the weight coefficient due to the variation of the specific scanning manner, which only needs to make corresponding adjustments according to the specific scanning manner, so it will not be discussed any more.

Moreover, it should also be pointed out that FIG. 3 only provides a specific manner of reconstructing the CT image of the ROI in accordance with the CT projection data of the ROI and the region B. Other methods utilizing the CT projection data of the ROI and the region B in light of the principle of the present invention may also be applicable, and all these methods fall within the protection scope of the present invention.

Figure 4:
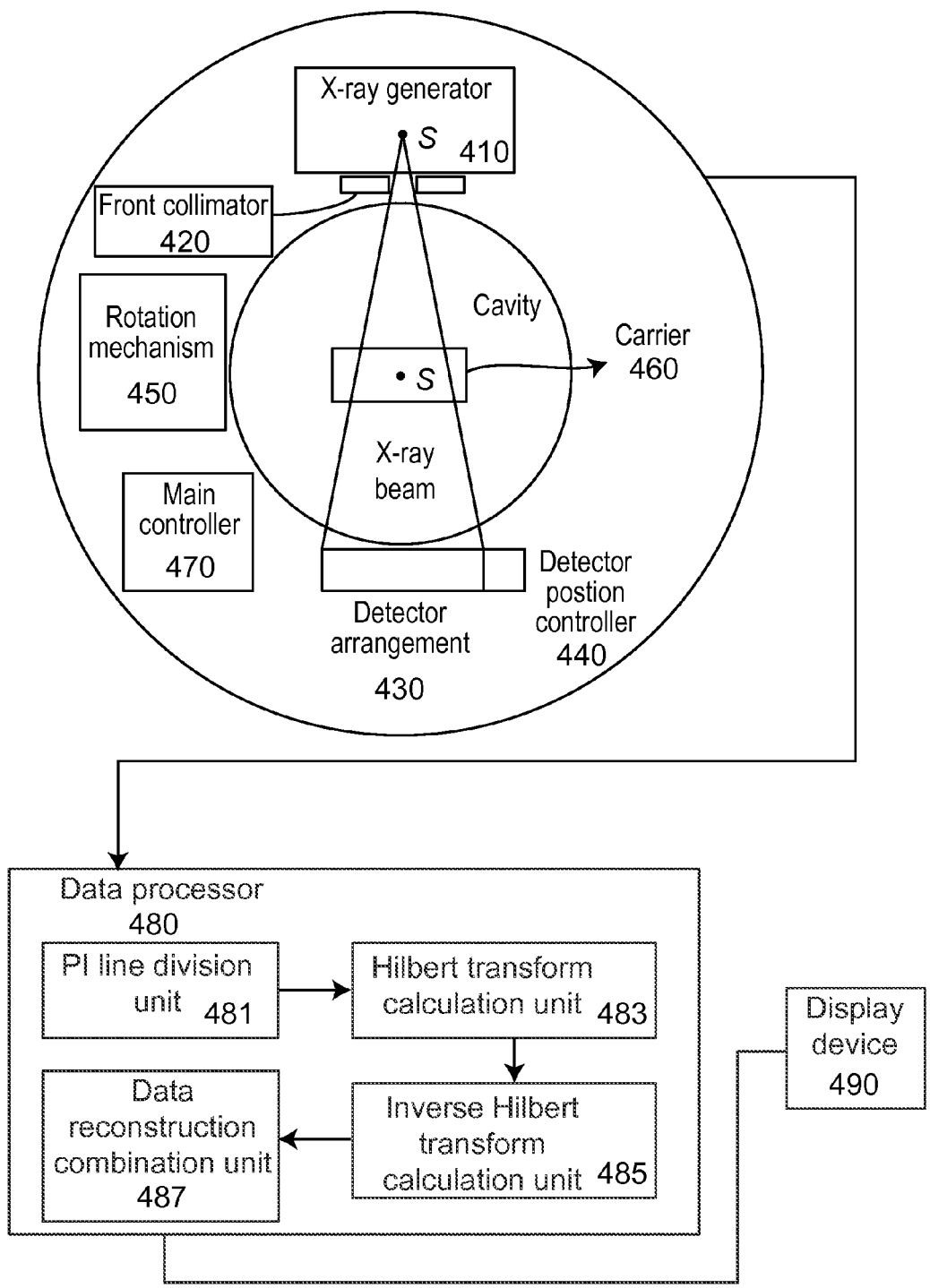
FIG. 4 shows a block diagram of a CT imaging device 400 according to an embodiment of the present invention.

FIG. 4 shows a CT imaging device 400 according to an embodiment of the present invention which performs CT imaging using the CT imaging method according to the present invention. The CT imaging device 400 comprises an X-ray generator 410 for generating an X-ray beam for use in scanning, a front collimator 420, detector arrangement 430, a detector position controller 440, a rotation mechanism 450, a carrier 460 of the object under examination, a main controller 470, a data processor 480 and display device 490.

Figure 5:
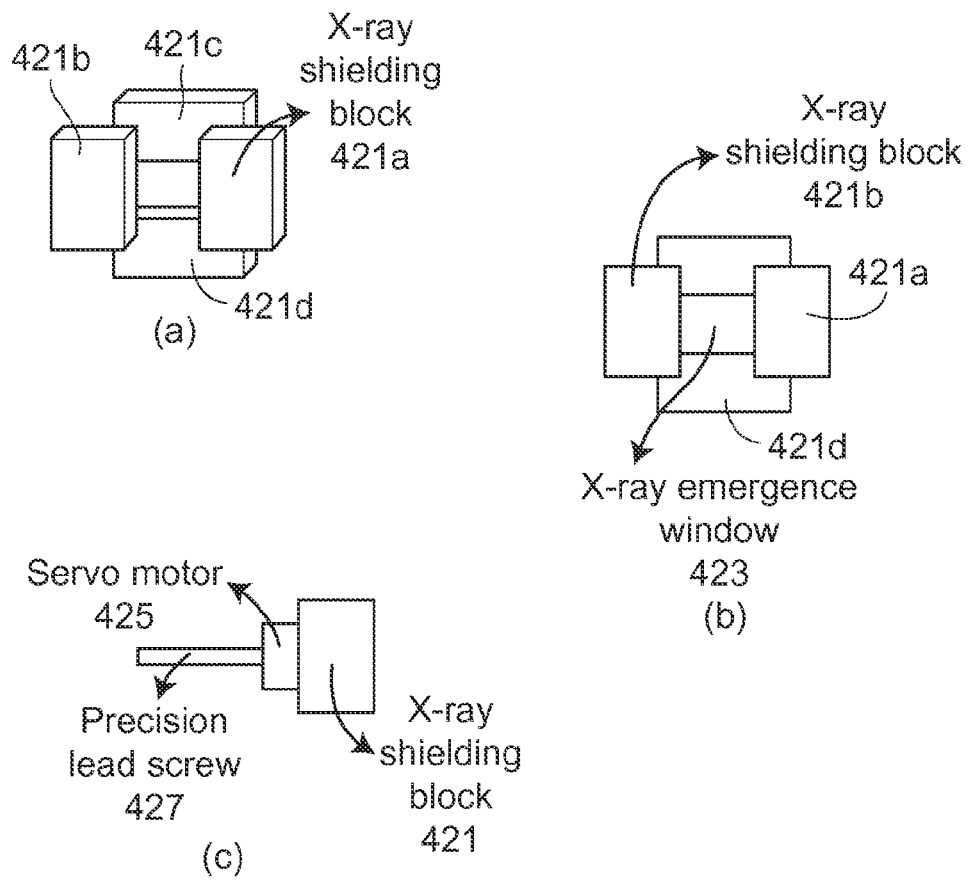
FIG. 5 shows a block diagram of a front collimator 420 in the CT imaging device 400 according to an embodiment of the present invention.

The X-ray emitted from the X-ray generator 410 is usually a sector beam (corresponding to a linear array detector) or a cone beam (corresponding to a planar array detector). The front collimator 420 is mounted at the position of a emergence window of the X-ray generator 410 for limiting the width of the X-ray beam, such that the width of the X-ray beam is consistent with the width of the detector in the detector arrangement. As stated in the CT imaging method described above, it is required to respective scan of the ROI and the region B, so it is necessary that the front collimator 420 has the function of adjusting the width of the X-ray beam such that the X-ray beam only covers the ROI or the region B. FIG. 5 shows the detailed structure of the front collimator 420. As shown in FIG. 5(a), the front collimator 420 is composed of four X-ray shielding blocks 421a-421d, forming an X-ray emergence window 423 of a certain shape, which can be circular, rectangular or other shapes. In this embodiment, as shown in FIG. 5(b), a rectangle is illustrated as an example. The X-ray shielding blocks 421a-421d are made of substances capable of effectively absorbing X-ray energy (which can be high density materials such as lead, tungsten etc.), and are thick enough to block the penetration of X-ray. Each X-ray shielding blocks 421a-421d is provided with a set of servo motors 425 and precision lead screws 427 operating independently and located behind of the blocks (as shown in FIG. 5(c)). The servo motor 425 and the precision lead screw 427 are capable of, driving corresponding X-ray shielding blocks 421a-421d to move forward or backward along the precision lead screw 427 in accordance with given parameters under the control of the main controller 470. As long as four sets of servo motor 425 and precision lead screw 427 operate simultaneously in accordance with the given parameters, the X-ray emergence window 423 will be able to change the size and position of the window correspondingly with respect to different ROI or region B, so as to meet the requirement that the X-ray only covers the ROI or the region B during the scanning. Of course, the number of the X-ray shielding blocks is not necessarily four, and any X-ray shielding blocks capable of forming an X-ray emergence window of a certain shape can fall within the protection scope of the present invention.

The detector arrangement 430 can adapt a linear array of detectors or a planar array of detectors, or a flat-panel detector with corresponding auxiliary devices. The detector arrangement 430 detects the X-ray passing through the scanned region to produce projection data and transmits the projection data to the data processor 480 for further processing by optical fiber cable, network cable, etc. wire or wirelessly.

Figure 6:
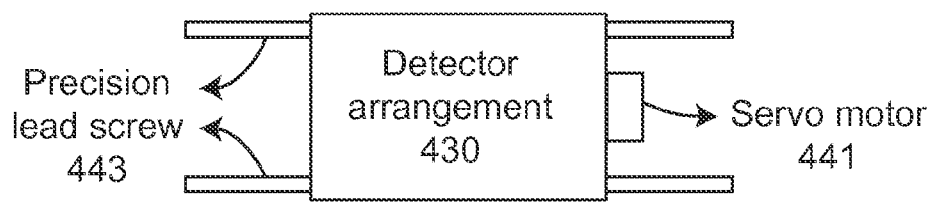
FIG. 6 shows a block diagram of a detector position controller 440 in the CT imaging device 400 according to an embodiment of the present invention.

The detector position controller 440 is used to control the position of the detector arrangement 430, and include the servo motor 441 and the precision lead screw 443 and so on. FIG. 6 explains the detailed structure of the detector position controller 440 in an embodiment where the detector arrangement 430 is a planar array detector. As shown in FIG. 6, the detector arrangement 430 is fixed to the precision lead screw 443 by means of a card slot, and the servo motor 441 drives the detector arrangement 430 to move in a straight line along the lead screw 443 under the control of the main controller 470. Since both the ROI and the region B are required to be selectable, it is necessary that scope of the movement of the detector arrangement 430 covers any selectable positions in the ROI and the region B. Therefore, it is possible that the position of the detector arrangement 430 is variable for each X-ray projection angle so as to change the position of the detector means 430 under the control of the main controller 270 as appropriate.

The rotation mechanism 450 comprises a can frame capable of rotating around a certain fixed center. The X-ray generator 410, the front collimator 420, the detector arrangement 430, the detector position controller 440, etc. are all mounted to the can frame. In the CT scanning, the can frame rotates together with the above components under the control of the main controller 470, and during the rotation, the X-ray generator 410 emits at different angles X-ray that passes through the region under examination (for instance the ROI or the region B) and is detected by the detector arrangement 430 from which the projection data is transmitted to the data processor 480 in the backend for processing. The rotation mechanism 450 can perform multi-loop rotating scanning, mono-loop rotating scanning or reciprocal multi-loop rotating scanning, as long as these scanning manners can enable the CT imaging device 400 to obtain enough projection data for image construction, and all these canning manners fall within the protection scope of the present invention. The carrier 460 of the object under examination carries the object under examination in and out of the CT imaging device 400, and its structure is similar to the current device. Usually, the carrier 460 of the object under examination is located in the vicinity of the rotating center of the rotation mechanism 450 and the ROI is usually a part of the object under examination.

The main controller 470 controls the entire scanning procedure. In the embodiments of the present invention, the main controller 470 controls the CT imaging device 400 in a manner corresponding to the CT imaging method illustrated in FIG. 2. The main controller 470 first controls the front collimator 420 and the detector position controller 440 based on the determined ROI such that the X-ray emitted from the X-ray generator 410 only covers the ROI. Then the main controller 470 controls the CT imaging device 400 to perform CT scanning of the ROI to acquire the projection data of the ROI and transmit the data to the data processor 480. Subsequently, the main controller 470 controls the front collimator 420 and the detector position controller 440 based on the determined region B such that the X-ray emitted from the X-ray generator 410 only covers the region B. Then, the main controller 470 controls the CT imaging device 400 to perform CT scanning of the region B to acquire the projection data of the region B and transmit the data to the data processor 480.

After the data processor 480 has acquired the projection data of the ROI and the region B, it reconstructs the image of the ROI in accordance with the reconstruction method illustrated in FIG. 3. Specifically, the data processor comprises PI line division unit 481, Hilbert transform calculation unit 483, inverse Hilbert transform calculation unit 485 and data reconstruction combination unit 487, wherein the PI line division unit 481 selects a group of PI line segments that can cover the ROI depending on the relative position of the ROI and the region B, and ensures that each PI line passing through the ROI also passes through the region B. The Hilbert transform calculation unit 483 calculates a one dimensional Hilbert transform value along the PI line for each PI line in the group. The inverse Hilbert transform calculation unit 485 performs limit inverse Hilbert transform for the one dimensional Hilbert transform value calculated by the Hilbert transform calculation unit 483, so as to acquire the reconstruction image values of the PI line segment, wherein in the inverse Hilbert transform calculation unit 485, a repeated iteration, i.e., the POCS iterative procedure, between the reconstruction image domain and the Hilbert transform space domain is required to acquire a reconstruction image satisfying the accuracy requirement. The data reconstruction combination unit 487 combines the reconstruction images calculated by the inverse Hilbert transform calculation unit 485 for each PI line in the group with respect to the group of PI lines provided by the PI line division unit 481 to obtain the result ROI image. The details of the processing in the data processor 480 have been discussed above, and hence it will not be discussed any more.

In addition, the data processor 480 further performs image data processing executed in traditional imaging device and CT scanning such as rigidification, scattering correction, metal artifacts correction and image processing and pattern recognition.

The display device 490 displays the reconstructed ROI image and it can further display information related to the control and the parameters during the CT scanning such that the operator can acquire the above information directly.

The CT imaging device 400 according to the present invention can reconstruct the ROI image rapidly and exactly by scanning the ROI and the region B respectively. Although two times of CT scanning are involved, only the ROI and the region B are to be scanned, so the scanning and reconstruction speed is improved instead. Beside, the region of the object under examination is less exposed to X-ray significantly.

It should be pointed out that although in the description of the embodiment with respect to the CT imaging device 400, the CT projection data of the ROI is acquired before the CT projection data of the region B being acquired, but this sequence can be arbitrary, for instance, the CT projection data of the region B can be acquired before the CT projection data of the ROI being acquired. Or even, in an embodiment according to the present invention, the CT projection data of the ROI and the region B can be acquired simultaneously. All these manners of acquiring the CT projection data of the ROI and the region B fall within the protection scope of the present invention.

Figure 7:
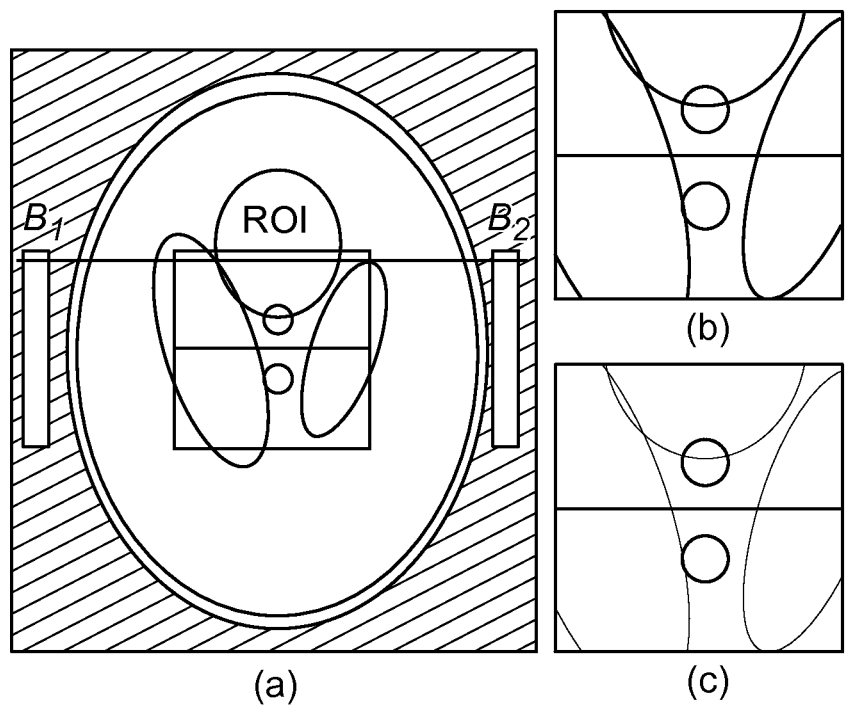
FIG. 7 shows the numerical simulation results of CT imaging with the CT imaging device according to an embodiment of the present invention.

FIG. 7 shows the numerical simulation results of CT image scanning and reconstruction with the CT imaging device according to the present invention. In the experiment, we adopted a Shepp-logan head model which was constrained in a circle with a diameter of 20 cm. The ROI was a square of side 6 cm placed at the center of the head model. Two elongated rectangles B1 and B2 were placed at the location of x=±8.0 cm respectively. It can be known from the definition of the head model that the image values in the elongated rectangles B1 and B2 are both 0. When the ROI underwent the CT scanning, a parallel beam X-ray only covers the ROI and the regions B1 and B2 during the 180 degree scanning, as shown in FIG. 7(*a*). FIG. 7(*b*) is an ROI image reconstructed with the projection data passing through the ROI and the regions B1 and B2 using the image reconstruction method according to the present invention; and FIG. 7(*c*) is an ROI image reconstructed only with the projection data passing through the ROI and the region B1 using the image reconstruction algorithm according to the present invention. It can be seen from the reconstruction results of (b) and (c) that with the CT imaging method of the present invention, an ROI image of high quality can be reconstructed when the X-ray only covers the ROI and a further small region outside of the object, which ROI image can satisfy the requirement of engineering applications. Furthermore, this CT imaging technique can save the size of the detector, reduce the amount of the projection data and improve the speed of CT image reconstruction to a considerable degree. What is more important, it can greatly decrease the X-ray radiation dose exposed on the object/patient while ensuring the quality of the ROI CT image, which is significant for medical CT imaging.

It should be noted that in the CT imaging device according to the present invention, components therein are logically divided in light of the functions to be achieved. However, the present invention is not limited by this and the components of the CT imaging device can be redivided or recombined upon needs, for instance, some components can be combined as an individual component or some components can be further divided into more sub-components.

The embodiments of the present invention can be carried out by hardware or by software modules run on one or more processors, or by the combination thereof. One skilled in the art should understand that microprocessors or digital signal processors (DSP) can be used in practice to carry out some or all of the functions of some or all of the components of the CT imaging device according to the embodiments of the present invention. The present invention can further be implemented as device or means programs (for example, computer programs and computer program products) for executing part or all of the method described herein. Such programs carrying out the present invention can be stored in a computer-readable medium, or have the form of one or more signals. Such signals can be downloaded from Internet websites or provided by a carrier signal or provided in any other forms.

It should be noted that the above embodiments illustrate rather than limit the invention, and that those skilled in the art will be able to design alternative embodiments without departing from the scope of the appended claims. In the claims, any reference signs placed between parentheses shall not be construed as limiting the claim. The word "comprise" does not exclude the existence of elements or steps other than those listed in a claim. The word "a" or "an" preceding an element does not exclude the existence of a plurality of such elements. The present invention can be achieved by means of hardware comprising several different elements and by means of an appropriately programmed computer. In unit claims listing several means, several of these means can be embodied by one and the same item of hardware. The use of ordinal words such as first, second and third does not represent any order, but instead, they can be understood as titles.

The invention claimed is:

1. A method of CT imaging a region of interest of an object under examination, comprising:
acquiring first CT projection data of the region of interest, wherein the region of interest is located within an object support with respect to the object, wherein the region of interest does not abut a perimeter of the object support, wherein the first CT projection data is acquired through a first CT scan, and wherein during the first CT scan the region of interest is adjusted into a scanning field of view such that an X-ray beam of the first CT scan only covers the region of interest;
acquiring second CT projection data of region B, wherein at least a part of the region B is located outside the object support, and wherein the region B is separate from the region of interest and the region B is selected to enable the selection of a group of PI line segments covering the region of interest, and each PI line segment passing through the region of interest passes through the region B, wherein the second CT projection data is acquired through a second CT scan, and wherein during the second CT scan region B is adjusted into the scanning field of view such that an X-ray beam of the second CT scan only covers the region B; and reconstructing the CT image of the region of interest based on the first CT projection data of the region of interest acquired in the first CT scan and the second CT projection data of the region B acquired in the second CT scan.

2. The CT imaging method according to claim 1, wherein the reconstruction of the CT image of the region of interest based on the first CT projection data of the region of interest acquired in the first CT scan and the second CT projection data of the region B acquired in the second CT scan comprises steps of:

for each PI line segment in the group of PI line segments:
calculating one dimensional Hilbert transform value of the PI line segment, and
performing a limit inverse Hilbert transform for the one dimensional Hilbert transform value to acquire the reconstruction image value of the PI line segment;
combining the reconstruction image values in all the PI lines in the group of PI line segments to obtain the image of the region of interest.

3. The CT imaging method according to claim 2, wherein the limit inverse Hilbert transform comprises step of:
performing Projection onto Convex Set (POCS) iteration between the reconstruction image domain and the Hilbert transform space domain to acquire a reconstruction image in the PI line segment that satisfies the accuracy requirement.

4. The CT imaging method according to claim 1, wherein the acquisition of the first CT projection data of the region of interest and the acquisition of the second CT projection data of the region B comprise:
performing CT scanning of the region of interest and the region B with parallel beam, sector beam or cone beam X-ray to acquire the first and second CT projection data of the region of interest and the region B respectively.

5. A non-transitory computer readable medium which stores instructions for implementing the steps of the method according to claims 1 when loaded to a computer and operated thereon.

6. A CT imaging device for CT imaging a region of interest of an object under examination, comprising:
an X-ray generator being configured to generate an X-ray beam for use in scanning;
a detector arrangement being configured to detect the X-ray passing through a scanned region so as to produce projection data;
a carrier of the object being configured to carry the object under examination in and out of the CT imaging device;
a main controller being configured to control the operation of the CT imaging device, such that a first X-ray emitted in a first CT scan from the X-ray generator only covers the region of interest so as to obtain first CT projection data of the region of interest, and such that a second X-ray emitted in a second CT scan from the X-ray generator only covers the region B so as to obtain second CT projection data of the region B, wherein the region of interest is located within an object support with respect to the object, the region of interest does not abut a perimeter of the object support, the region B is located outside the object support, wherein the region B is selected to enable the selection of a group of PI line segments covering the region of interest, and wherein each PI line segment passing through the region of interest also passes through the region B; and
a data processor being configured to reconstruct the image of the region of interest based on the first CT projection data of the region of interest acquired in the first CT scan and the second CT projection data of the region B acquired in the second CT scan.

7. The CT imaging device according to claim 6, wherein the data processor comprises:
PI line division unit being configured to provide a group of PI line segments covering the region of interest;
Hilbert transform calculation unit being configured to calculate a one dimensional Hilbert transform value along the PI line segment for each PI line segment in the group of PI line segments;
inverse Hilbert transform calculation unit being configured to perform limit inverse Hilbert transform for the one dimensional Hilbert transform value calculated by the Hilbert transform calculation unit, so as to acquire the reconstruction image value in the PI line segment; and
data reconstruction combination unit being configured to combine the reconstruction images calculated by the inverse Hilbert transform calculation unit for each PI line to obtain the image of the region of interest.

8. The CT imaging device according to claim 7, wherein the inverse Hilbert transform calculation unit performs Projection onto Convex Set (POCS) iteration between the reconstruction image domain and the Hilbert transform space domain to acquire a reconstruction image for the PI line segment that satisfies the accuracy requirement.

9. The CT imaging device according to claim 6, further comprising:
a front collimator being configured to adjust the width of the first and second X-ray beams under the control of the main controller such that the first and second X-ray beams only covers the region of interest or the region B respectively.

10. The CT imaging device according to claim 9, wherein the front collimator comprises a plurality of X-ray shielding blocks forming an X-ray emergence window of a certain shape, which X-ray shielding blocks can cooperate to change the size and the position of the X-ray emergence window.

11. The CT imaging device according to claim 10, wherein the front collimator comprises four X-ray shielding blocks, each of which is controlled by a set of servo motors and precision lead screws operating independently, such that the X-ray shielding blocks move along the precision lead screw.

12. The CT imaging device according to claim 6, further comprising:
a detector position controller being configured to control the position of the detector means such that the movement scope of the detector means can cover the positions of the region of interest and the region B.

13. The CT imaging device according to claim 12, wherein the detector position controller comprises a servo motor and a precision lead screw, wherein the detector arrangement is fixed on the precision lead screw so that it is driven by the servo motor to move along the precision lead screw.

* * * * *